(12) United States Patent
Swett et al.

(10) Patent No.: US 8,970,093 B2
(45) Date of Patent: Mar. 3, 2015

(54) PIEZOELECTRIC TRANSDUCER FOR MEASURING FLUID PROPERTIES

(75) Inventors: Dwight W. Swett, Houston, TX (US); Holger C. Stibbe, Humble, TX (US)

(73) Assignee: Baker Hughes Incorporated, Houston, TX (US)

( * ) Notice: Subject to any disclaimer, the term of this patent is extended or adjusted under 35 U.S.C. 154(b) by 542 days.

(21) Appl. No.: 13/411,710

(22) Filed: Mar. 5, 2012

(65) Prior Publication Data
US 2013/0063000 A1 Mar. 14, 2013

Related U.S. Application Data

(60) Provisional application No. 61/453,323, filed on Mar. 16, 2011.

(51) Int. Cl.
*H01L 41/09* (2006.01)
*H01L 41/053* (2006.01)
*E21B 49/08* (2006.01)

(52) U.S. Cl.
USPC ......... 310/348; 310/328; 310/338; 73/152.28

(58) Field of Classification Search
USPC ............... 310/311, 328, 338, 348; 73/152.28; 367/30, 31, 166
See application file for complete search history.

(56) References Cited

U.S. PATENT DOCUMENTS

| | | | |
|---|---|---|---|
| 2,425,869 A * | 8/1947 | Dillon | 324/355 |
| 3,213,414 A * | 10/1965 | Moser | 181/106 |
| 3,743,869 A | 7/1973 | Hugli | |
| 3,960,018 A * | 6/1976 | Change et al. | 73/723 |
| 4,550,744 A * | 11/1985 | Igashira et al. | 137/80 |
| 4,594,584 A | 6/1986 | Pfieffer et al. | |
| 4,638,872 A | 1/1987 | Park et al. | |
| 4,701,600 A * | 10/1987 | Beech et al. | 235/375 |
| 5,139,087 A | 8/1992 | Hutchins et al. | |
| 5,515,733 A * | 5/1996 | Lynnworth | 73/861.27 |
| 6,938,470 B2 | 9/2005 | DiFoggio et al. | |
| 7,195,063 B2 | 3/2007 | Nogueira et al. | |
| 7,322,251 B2 | 1/2008 | Gysling et al. | |
| 7,703,317 B2 | 4/2010 | Goodwin et al. | |
| 7,811,525 B2 | 10/2010 | Laugharn, Jr. et al. | |
| 7,845,219 B2 | 12/2010 | Goodwin et al. | |
| 2005/0044966 A1 | 3/2005 | Gysling et al. | |
| 2008/0066536 A1 | 3/2008 | Goodwin et al. | |
| 2008/0257036 A1 | 10/2008 | Chaudoreille et al. | |
| 2010/0011845 A1 | 1/2010 | Laugharn, Jr. et al. | |
| 2010/0294028 A1* | 11/2010 | Siegenthaler et al. | 73/114.16 |
| 2011/0314933 A1* | 12/2011 | Mueller et al. | 73/861.18 |

OTHER PUBLICATIONS

International Search Report and Written Opinion dated Dec. 27, 2012 for Application No. PCT/US2012/029461.
S. Kostek, et al.; "Modeling of a Piezoelectric Transducer and its Application to Full Waveform Acoustic Logging"; J. Acoust. Soc. Am.; vol. 95, Issue 1; Jan. 1994.

\* cited by examiner

*Primary Examiner* — Thomas Dougherty
(74) *Attorney, Agent, or Firm* — Cantor Colburn LLP

(57) ABSTRACT

A transducer includes a preload adapter having a sleeve portion and an end and a housing including a seating portion and a shaft portion that extends from the seating portion. The transducer also includes a piezoelectric element contained at least partially within a chamber that is at least partially defined by the sleeve portion and shaft portion and a diaphragm coupled to an external side of the end such that motion of the piezoelectric element causes motion of the diaphragm.

20 Claims, 5 Drawing Sheets

PIEZOELECTRIC TRANSDUCER FOR MEASURING FLUID PROPERTIES

PRIORITY CLAIM

This application claims priority under 35 U.S.C. §119(e) to U.S. Provisional Patent Application Ser. No. 61/453,323, filed Mar. 16, 2011, entitled PIEZOELECTRIC TRANSDUCER FOR MEASURING FLUID PROPERTIES, and which is hereby incorporated by reference in its entirety.

BACKGROUND

1. Field of the Invention

The present invention generally relates to instruments for measuring fluid properties and, particularly, to a piezoelectric transducer for measuring properties of borehole fluids.

2. Description of the Related Art

In underground drilling applications, such as oil and gas exploration and recovery, a borehole is drilled into the earth. The drilling process can include taking measurements of fluids in the borehole while the borehole is being drilled (logging while drilling (LWD)). In some cases, a wireline is used to lower a measurement instrument into the borehole after a stage of the drilling process has been completed to measure properties of fluids in the borehole.

Measured fluid properties can include, for example, the density and viscosity of the fluid. The properties can be measured by placing a mechanical oscillator in the flow path of the fluid. Fluid density is measured primarily by measuring changes in the vibrational frequency of the oscillator while viscosity is determined primarily by monitoring the decay time of the resonance.

Other properties can be measured either directly or indirectly by utilizing speed of sound measurements taken in the fluid. These measurements are typically referred to as "sound speed" measurements and can be used, for example, to determine a gas-to-oil ratio (GOR) of the fluid.

Presently, there exist devices that can measure two of three of sound speed, density and viscosity. In particular, instruments exist that can measure density and viscosity or that can measure density and sound speed. Instruments that can be used to measure all three do not.

BRIEF SUMMARY

According to one embodiment, a transducer that includes a preload adapter having a sleeve portion and an end and a housing including a seating portion and a shaft portion that extends from the seating portion is disclosed. In this embodiment, the transducer further includes a piezoelectric element contained completely within a chamber that is defined by the sleeve portion and shaft portion and a diaphragm coupled to an external side of the end such that motion of the piezoelectric element causes motion of the diaphragm.

According to another embodiment, an instrument for measuring properties of a borehole fluid that includes a body, a fluid chamber formed within the body and providing a fluid path at least partially through the instrument and a transducer mounted in the body and having a movable diaphragm located at least partially within the fluid chamber is disclosed. The transducer in this embodiment includes a preload adapter having a sleeve portion and an end, a housing including a seating portion and a shaft portion that extends from the seating portion and a piezoelectric element contained completely within a chamber that is at least partially defined by the sleeve portion and shaft portion. The diaphragm in this embodiment is coupled to an external side of the end such that motion of the piezoelectric element causes motion of the diaphragm.

According to yet another embodiment, a transducer that includes a sleeve portion having an end, a housing including a seating portion and a shaft portion that extends from the seating portion and a piezoelectric element contained at least partially within a chamber that is at least partially defined by the sleeve portion and shaft portion such that the piezoelectric element does not contact a fluid during a sampling operation is disclosed. The transducer of this embodiment also includes a diaphragm coupled to an external side of the end such that motion of the piezoelectric element causes motion of the diaphragm.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures. In particular, disclosed herein is a transducer that can be utilized to measure one or all of density, viscosity and sound speed of a fluid. In the following description the fluid being examined shall be assumed to be a fluid existing in or that can be extracted from a wall of a borehole penetrating the earth but the transducer disclosed herein could be utilized on other fluids as well. Further, while a transducer is particularly described, it shall be understood that embodiments of the present invention can extend to any instrument that carries a transducer as disclosed herein or equivalents thereof.

Figure 1:
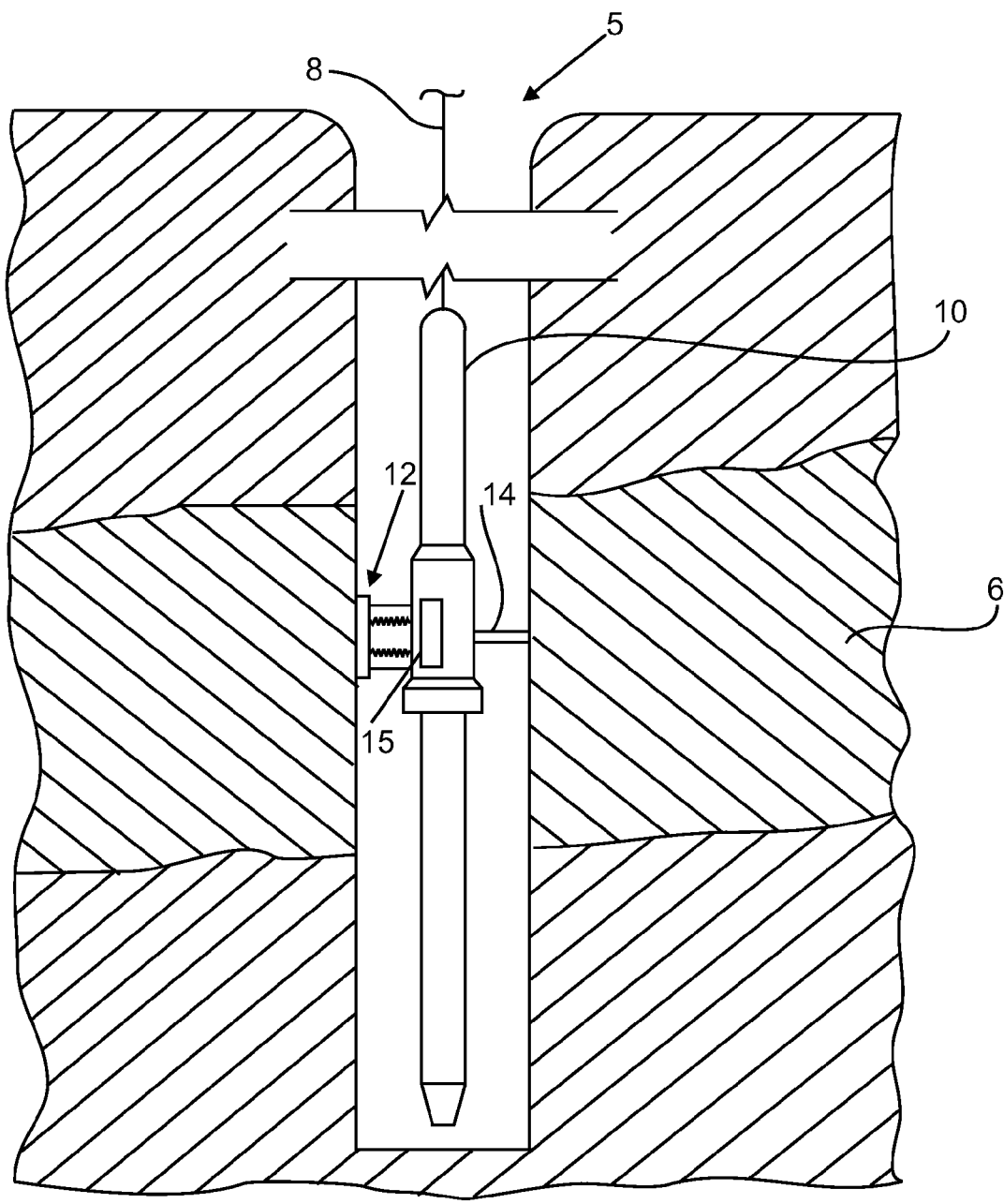
FIG. 1 illustrates an instrument deployed into a borehole.

Referring now to FIG. 1, fluid sampling in the borehole environment generally involves disposing an instrument 10 into a borehole 5 via a wireline 8. Oppositely located on the outer portion of the instrument 10 are a sample port 14 and an urging means 12. When the sample port 14 is proximate to a formation of interest 6, the urging means 12 is extended against the inner surface of the borehole 5 thereby engaging the sample port 14 into the formation 6. The engagement of the sample port 14 pierces the outer diameter of the borehole 5 and enables fluid communication between the fluid in the formation 6 and the sample port 14. The instrument 10 can also include a sample channel 15 though which the fluid contacting the sample port 14 can be drawn by a pump or other device in a manner such that it flows through the sample channel 15. Measurements of the properties of the fluid can be measured by one or more measurement instruments disposed in or around the sample channel 15. As discussed in greater detail below, a transducer according to an embodiment can be arranged with respect to the sample channel 15 in a manner that allows it to be used to measure one or more of the density, viscosity and sound speed of a fluid.

It shall be understood that the wireline 8 can be connected to a drilling rig and include a stress member and various conductors for transmitting commands to the instrument 10, for receiving data from the instrument 10 as well as providing power. The wireline 8, as such, can be coupled to an electronics module (e.g., a computing device), and allow for the transmission of required operating commands to the instrument 10 for bi-directional data transfer. The data may be recorded on an archival storage medium of any desired type for concurrent or later processing. The data may be transmitted in analog or digital form. Data processors such as a suitable computer may be provided for performing data analysis in the field in real time or the recorded data may be sent to a processing center or both for post processing of the data.

Figure 2:
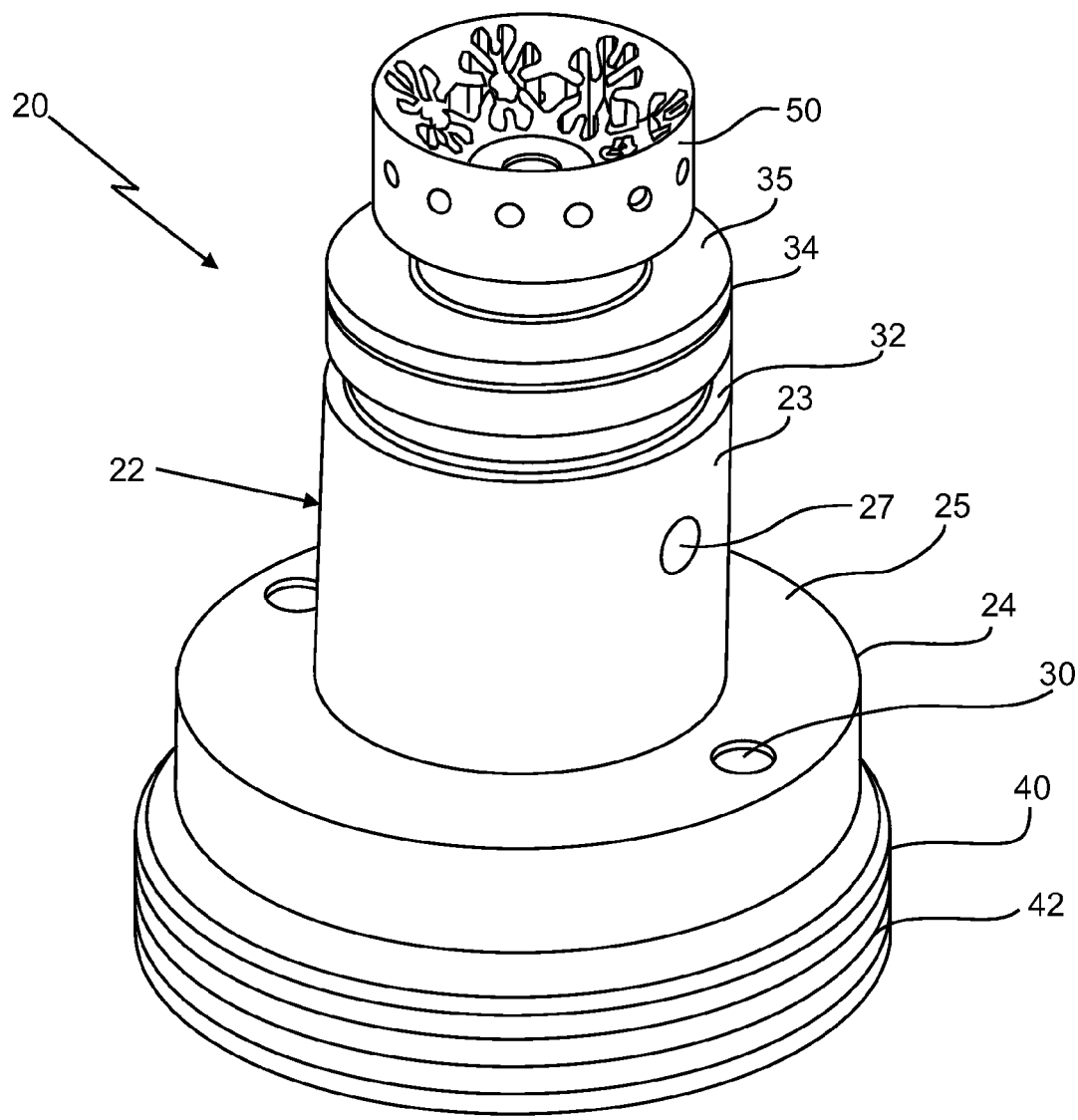
FIG. 2 is a perspective view of a transducer according to one embodiment.

FIG. 2 is a perspective view of a transducer 20 according to one embodiment. The transducer 20 can be arranged within or on the instrument 10 shown in FIG. 1 such that it can perform measurements on the fluid passing through the sample channel 15. In one embodiment, the transducer 20 is a piezoelectric transducer as described in greater detail below. Generally, a piezoelectric transducer is a transducer that includes one or more piezoelectric elements.

The transducer 20 illustrated in FIG. 2 includes a housing 22. As illustrated, the housing 22 includes a shaft portion 23 coupled to a seating portion 24. The shaft portion 23 extends away from a mating surface 25 of the seating portion 24. The shaft portion 23 can be cylindrical as illustrated in FIG. 2 or any other shape. The shaft portion 23 surrounds at least a portion a piezoelectric element in one embodiment. As illustrated, the shaft portion 23 has an outer diameter that is smaller than the diameter of the seating portion 24. In this manner, the shaft portion 23 can extend into a hole in a measurement instrument while the seating portion 24 (and particularly, the upper surface 25) is rotationally secured with respect to a surface surrounding the hole. In one embodiment, the seating portion 24 includes one or more fastening holes 30 through which a bolt (preferably unthreaded) or other rigid member can pass to prevent rotation of the housing 22 relative to the surface surrounding the hole. The hole into which the shaft portion 23 extends can provide access, for example, to a fluid passing though a sample channel 15 (FIG. 1).

The shaft portion 23 includes one or more access holes 27 through which a wire or other conductor can pass in order to carry a voltage or current to the piezoelectric element within the housing 22. In one embodiment, the access holes 27 also allow a wire or other conductor to carry a voltage or current away from the piezoelectric element. Of course, the number of holes 27 in the shaft portion 23 can be varied from that shown ni FIG. 2 depending on the particular implementation and can be omitted in some instances. In one embodiment, the holes 27 can be moved to another location in the housing 22. The shaft portion 23 may optionally include a sealing groove 32 into which a sealing o-ring or other sealing mechanism may be inserted The transducer 20 also includes a preload adapter 34. The preload adapter 34 provides a mechanism by which the piezoelectric element within the shaft portion 23 can be loaded in compression. To that end, the preload adapter 34 can be threaded or otherwise mated to the shaft portion 23 in order to impart a preload compressive force on the piezoelectric element within the housing 22. The preload adapter 34 includes a mating face 35 configured to mate with an inner shoulder in the hole into which the shaft portion 23 is inserted.

The transducer 20 also includes a sensor retaining device 40. Sensor retaining device includes mating features illustrated as threads 42 that allow it to force the housing 22 towards the preload adapter 34.

The transducer further includes a diaphragm 50. In operation, the diaphragm 50 is exposed to a fluid in the sample channel 15 (FIG. 1). The diaphragm 50 serves to translate an oscillation created by the piezoelectric element into a fluid in the sample channel 15 (FIG. 1) without the piezoelectric element being exposed to or otherwise in contact with the fluid. In addition, in one embodiment, the diaphragm 50 can be utilized to sense the resistance (impedance) of the fluid to the oscillation of the piezoelectric element. Further details of the diaphragm 50 are discussed below.

Figure 3:
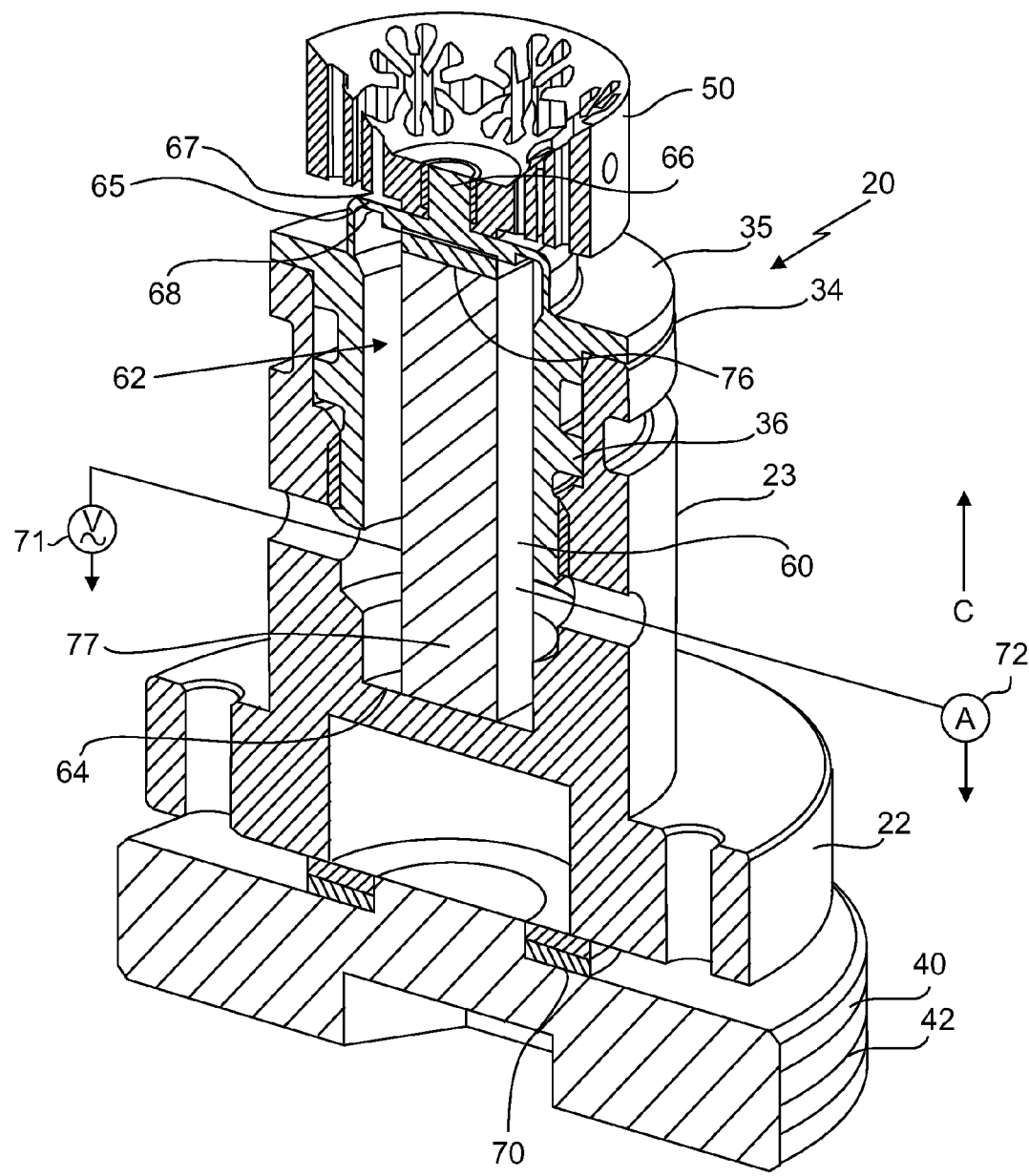
FIG. 3 is a cut-away side view of the transducer shown in FIG. 2.

FIG. 3 is a cut-away side view of the transducer 20 illustrated in FIG. 2. In the illustrated embodiment, a piezoelectric element 60 is disposed with a chamber 62 formed within the preload adapter 34 and the shaft portion 23. The piezoelectric element 60 is completely enclosed within the chamber 62 in one embodiment.

As illustrated, the preload adapter 34 includes an inner sleeve portion 36 configured to extend into an inner diameter of the sleeve portion 23. The depth which the inner sleeve portion 36 extends into the shaft portion 23 can vary depending on the application. The inner sleeve portion 36 is fixedly attached to the sleeve portion 23 to impart the preload compression on the piezoelectric element 60. In one embodiment, the inner sleeve portion 36 has an outer diameter that is smaller than the inner diameter of the sleeve portion 23. It shall be understood, however, that the preload adapter 34 could surround a portion of the sleeve portion 23. In such a case, the inner diameter of the inner sleeve portion 36 could be greater than the outer diameter of the sleeve portion 23.

The preload adapter 34 includes a mating surface 65. An external side 67 of the mating surface 65 is coupled to the diaphragm 50. In one embodiment, the external side 67 can include a boss 66 or other implement extending from it to which the diaphragm 50 can be attached. Of course, the boss 66 can be omitted and the diaphragm 50 can be directly connected to the external side 67 of the mating surface 65. Of course, the mating surface 65 can have varying thickness across its diameter to accommodate measurement accuracy while maintaining structural integrity.

The mating surface 65 of the preload adapter 34 also includes an internal side 68 that can be utilized to either directly or indirectly apply pressure to the piezoelectric element 60. The shaft portion 23 also includes an inner shelf member 64. In one embodiment, the piezoelectric element 60 is contained between the inner shelf member 64 and the internal side 68 of the mating surface 65 of the preload adapter 34.

Of course, the exact configuration of the shaft portion 23 and the preload adapter 34 can be varied from that shown in FIG. 3. Regardless of the exact configuration, the housing 22 and the preload adapter 34 cooperate to impart a compressive force on the piezoelectric element 60.

A preload spring 70 is displaced between the retaining mechanism 40 and the housing 22. Rotational motion of the retaining mechanism 40 will cause the housing 22 to travel towards the inner shelf due to threads 42. This motion compressing preload spring 70 urges housing 22 in the direction indicated by arrow C. In effect, the causes a preload to be created between surface 35 and the inner shelf.

Any type of piezoelectric element 60 can be utilized. In general, piezoelectricity is characterized by the ability of certain crystals to develop an electrical charge when subjected to mechanical stress. This behavior is denoted as the direct piezoelectric effect. Conversely, these crystals undergo a deformation when subjected to an electric potential field. This behavior is denoted as the inverse piezoelectric effect. The piezoelectric effect is exhibited by certain ceramic materials belonging to the ferroelectric group (e.g., lead zirconate titanate (PZT) consisting of mixed crystals of $PbZrO_3$ and $PbTiO_3$). The piezoelectric element 60 can be formed of any crystals or combination of crystals that exhibit the piezoelectric effect as long as the resulting structure can convert mechanical quantities, such as stress and strain, into electrical voltage and, conversely, transform electrical voltages into mechanical forces and displacements.

In one embodiment, the inverse piezoelectric effect can be created by coupling a voltage supply 71 to the piezoelectric element 60. Similarly, a current meter 72 can be utilized to measure the current produced due to compression/expansion of the piezoelectric element 60 due to the piezoelectric effect. In operation, and as described briefly above, the piezoelectric element 60 is preloaded. The magnitude and frequency of the voltage provided by the voltage supply 71 to the piezoelectric element 60 controls the travel distance and the frequency with which the diaphragm 50 moves in the fluid. The current meter 72 can measure the current flowing (I) from the piezoelectric element 60. The relative displacement of ends of the piezoelectric element 60 follow the received charge (Q) with good linearity and, as a consequence, the flowing current (I=dQ/dt) is proportional to the relative velocity of the ends (76, 77) of the piezoelectric element 60 (v=ds/dt). Accordingly, the steepness (slew-rate) of fluctuations in the current (dI/dt) are proportional to the relative acceleration (a=dv/dt) of the ends 76, 77.

In operation, when driven by voltage supply 71, the resulting displacement response of piezoelectric element 60 is a complex function of the applied voltage and the coupled interaction of boundary reaction forces. The boundary reaction forces are based, at least in part, on one or more of the density, viscosity and sound speed of a liquid to which the diaphragm 50 is exposed. In more detail, the boundary reaction forces develop a counter-acting strain that modify the relative displacement of the ends 76, 77 from the expected no-load (direct piezoelectric effect) response. The modification in relative displacement of the ends 76, 77 of the piezoelectric element 60 due to the combination of applied voltage and reaction force generally trends in a relationship with reaction force from the no-load condition. In this manner, the voltage provided by voltage source 60 and the currents read by the current meter 72 can be used to analyze one or more of the density, viscosity and sound speed of a fluid.

In prior applications, piezoelectric sensors have been used to determine the physical properties of fluid. For example, acoustic wave sensors have been developed based on mechanical resonance, including thickness-shear mode (TSM) resonators or surface-acoustic-wave (SAW) resonators. All of these resonators had the contact with the fluid being sampled. In contrast, according to one or more embodiments of the present invention, the piezoelectric element does not contact the fluid being sampled. This can be advantageous because the impedance response of a piezoelectric resonator is strongly affected by the fluid conductivity when its electrodes are located on the surface of the fork and the fork is immersed in a conductive fluid. This is because the conductive fluid is coupled to the piezoelectric resonator as a low-impedance parallel component in a circuit. The impedance response is still affected even when the electrodes are coated by a thin (tens to hundreds of microns) layer of dielectric materials. Consequently, they are only capacitively coupled to the fluid. In such cases, it is almost impossible to accurately measure the densities and viscosities of conductive or ionic fluids. By separating the piezoelectric element from the fluid being sampled, the inaccuracies caused by contact between the element and the fluid can be reduced or eliminated.

Figure 4:
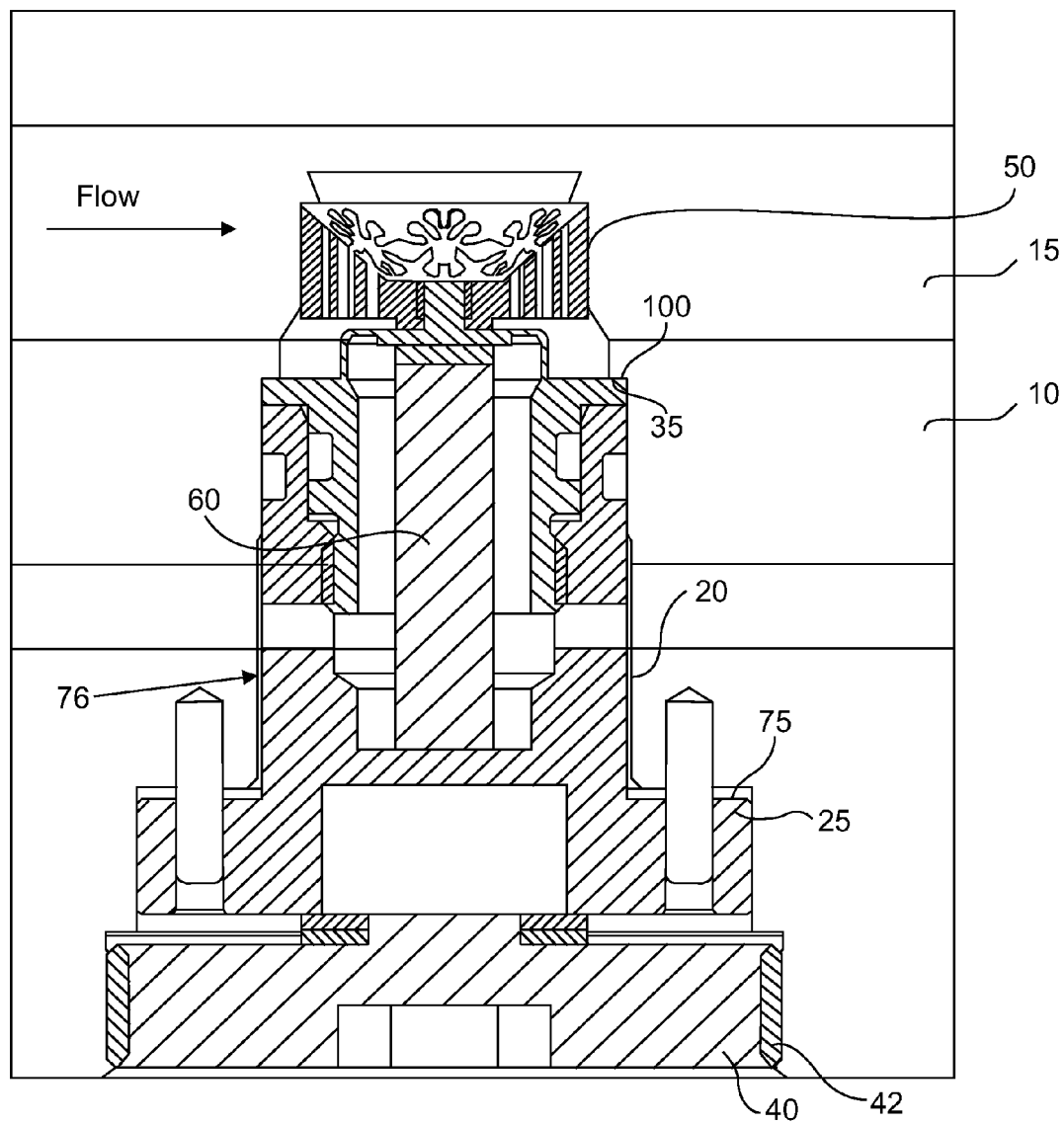
FIG. 4 shows a cut-away side view of the transducer shown in FIG. 2 installed into an instrument.

FIG. 4 shows a cut-away side view of a transducer 20 having its diaphragm 50 presented into a fluid chamber 15 of an instrument 10. As illustrated, the instrument includes an inner shelf 100 that contacts the mating face 35. As described above, the retaining mechanism 40 includes mating features 42 that mate with the instrument 10 and allow it urge the housing 22 towards inner shelf 100 and, thereby place a compressive force oncsurface 35 mating with shoulder 100. Application of a voltage to the piezoelectric element 60 causes the diaphragm 50 to oscillate in the fluid chamber 15. Of course, the fluid in the chamber will oppose such oscillations. This opposition will result in a modification of current that can be measured as described above. In one embodiment, the upper surface 25 does not contact a surface 75 that surround a hole 76 into which the transducer 20 is inserted.

Figure 5:
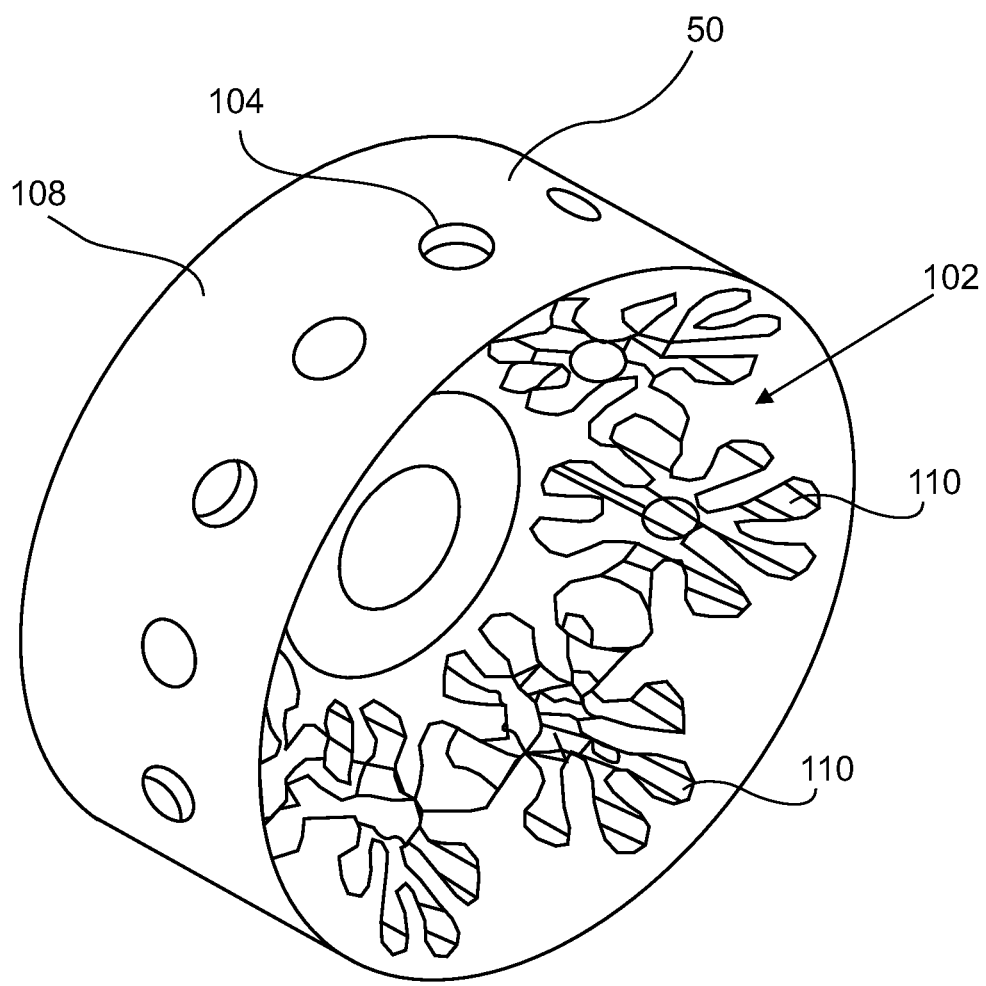
FIG. 5 is a perspective view of an example of diaphragm that can be utilized with an embodiment of a transducer.

FIG. 5 is a perspective view of an embodiment of a diaphragm 50. As described generally above, excitation of a piezoelectric element 60 (FIGS. 3-4) imparts linear motion the diaphragm 50 when it is coupled to the preload adapter 34 and a fluid being examined opposes that motion. The amount by which the linear motion is opposed can be, in some instances, measured and utilized to determine viscosity, density and sound speed of the liquid in the flow chamber. For viscosity measurements, the diaphragm 50 is preferably shaped such that it imparts a shearing force on the fluid while minimizing the turbulence it imparts because turbulence can create unwanted effects on the linear motion of the diaphragm. In one embodiment, this can be accomplished if the Reynolds number for the boundary layer flow over the diaphragm 50 can be maintained at a sufficiently low value over the range of fluid density and viscosity values to be measured. This is accomplished if the product of shearing surface transverse characteristic length and fluid velocity are below some threshold value. Practically, this can be accomplished by providing a recessed area 102 and through-cut perturbations 110 formed within the diaphragm 50. To promote fluid flow and to minimize obstruction due to sedimentation through the diaphragm 50 it may include holes 104 formed on its side 108. However, sufficient viscous work in the fluid needs to be developed to establish a highly correlated feedback in the measurement of fluid viscosity. To this end, the recessed area 102 can include one or more perturbations 110 formed on its surface and extending though diaphragm 50 as shown in FIG. 4. The shape of the perturbations 110 can vary and, in some cases, they can be aligned with the holes 104. As illustrated, the perturbations 110 are in a snowflake configuration. Regardless of the shape, in one embodiment, the perturbations 110 are formed such that the maximum Reynolds number is kept below 100 for the extreme in values expected for fluid sample parameters (e.g., density=300-1500 $kg/m^3$, viscosity=0.1-100 centipoise). In one embodiment, the perturbations 110 are formed by scoring a surface of the recessed area. In another embodiment, the perturbations pass entirely through the diaphragm 50.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second," and "third" are used to distinguish elements and are not used to denote a particular order.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A transducer comprising:
a preload adapter having a sleeve portion and an end;
a housing including a seating portion and a shaft portion that extends from the seating portion;
a piezoelectric element contained completely within a chamber that is defined by the sleeve portion and shaft portion; and
a diaphragm coupled to an external side of the end such that motion of the piezoelectric element causes motion of the diaphragm.

2. The transducer of claim 1, further comprising:
a retaining mechanism on an opposite side of the seating portion from the shaft portion; and
a preload spring disposed between the retaining mechanism and the seating portion.

3. The transducer of claim 2, wherein the retaining mechanism includes mating features configured to mate with corresponding mating features in an instrument.

4. The transducer of claim 1, wherein the preload adapter and the housing are arranged and configured to apply a compressive force on the piezoelectric element.

5. The transducer of claim 4, wherein the housing includes an inner shelf formed within the sleeve portion that defines a first end of the chamber and wherein the end of the preload adapter defines a second end of the chamber and wherein variation of a distance between the first end and the second end causes the compressive force to be applied.

6. The transducer of claim 1, in combination with a voltage supply configured to provide a voltage to the piezoelectric element.

7. The transducer of claim 1, in combination with a current meter configured to measure a current produced by the piezoelectric element.

8. The transducer of claim 1, wherein the diaphragm includes a recessed area formed therein.

9. The transducer of claim 8, wherein the recessed area includes one or more perturbations passing from a surface of the recessed area to an exterior of the diaphragm.

10. The transducer of claim 1, wherein the diaphragm includes one or more holes formed in a sidewall thereof.

11. The transducer of claim 10, wherein the diaphragm includes a recessed area that includes one or more perturbations formed on a surface thereof and wherein at least one of the perturbations is formed over one of the holes.

12. The transducer of claim 1, wherein the end of the preload adapter has at least two different thicknesses.

13. An instrument for measuring properties of a borehole fluid, the instrument comprising:
a body;
a fluid chamber formed within the body and providing a fluid path at least partially through the instrument; and
a transducer mounted in the body and having a movable diaphragm located at least partially within the fluid chamber, the transducer including:
a preload adapter having a sleeve portion and an end;
a housing including a seating portion and a shaft portion that extends from the seating portion; and
a piezoelectric element contained completely within a chamber that is at least partially defined by the sleeve portion and shaft portion;
wherein the diaphragm is coupled to an external side of the end such that motion of the piezoelectric element causes motion of the diaphragm.

14. The instrument of claim 13, wherein the body includes an inner shelf that contacts the preload adapter.

15. The instrument of claim 14, wherein the transducer further includes:
a retaining mechanism on an opposite side of the seating portion from the shaft portion and including mating features configured to mate with the body; and
a preload spring disposed between the retaining mechanism and the seating portion;
wherein mating the retaining mechanism with the body causes the preload spring to urge the preload adapter toward the inner shelf and to create a compressive force between them.

16. The instrument of claim 13, further comprising:
a voltage supply coupled to the piezoelectric element.

17. The instrument of claim 1, wherein the end of the preload adapter has at least two different thicknesses.

18. A transducer comprising:
a sleeve portion having an end;
a housing including a seating portion and a shaft portion that extends from the seating portion;
a piezoelectric element contained at least partially within a chamber that is at least partially defined by the sleeve portion and shaft portion such that the piezoelectric element does not contact a fluid being sampled during a sampling operation; and
a diaphragm coupled to an external side of the end such that motion of the piezoelectric element causes motion of the diaphragm.

19. The transducer of claim 18, wherein the sleeve portion is part of a preload adapter the preload adapter and the housing are arranged and configured to apply a compressive force on the piezoelectric element.

20. The transducer of claim 18, further comprising:
a retaining mechanism on an opposite side of the seating portion from the shaft portion and including mating features configured to mate an instrument; and
a preload spring disposed between the retaining mechanism and the seating portion;
wherein mating the retaining mechanism with the instrument causes the preload spring to urge the preload adapter towards an inner shelf within the instrument and to create a compressive force between them.

* * * * *